United States Patent
Ichitani

(10) Patent No.: US 10,451,554 B2
(45) Date of Patent: Oct. 22, 2019

(54) IMAGE PROCESSING DEVICE, IMAGE PROCESSING METHOD, AND RECORDING MEDIUM STORING COMPUTER READABLE IMAGE PROCESSING PROGRAM

(71) Applicant: KONICA MINOLTA, INC., Chiyoda-ku (JP)

(72) Inventor: Shuji Ichitani, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 14 days.

(21) Appl. No.: 15/551,374

(22) PCT Filed: Feb. 8, 2016

(86) PCT No.: PCT/JP2016/053615
§ 371 (c)(1),
(2) Date: Aug. 16, 2017

(87) PCT Pub. No.: WO2016/136441
PCT Pub. Date: Sep. 1, 2016

(65) Prior Publication Data
US 2018/0038796 A1    Feb. 8, 2018

(30) Foreign Application Priority Data

Feb. 23, 2015   (JP) .................. 2015-032538

(51) Int. Cl.
*G01N 21/64*        (2006.01)
*G06T 7/00*         (2017.01)
(Continued)

(52) U.S. Cl.
CPC ......... *G01N 21/6458* (2013.01); *G01N 21/64* (2013.01); *G01N 33/48* (2013.01);
(Continued)

(58) Field of Classification Search
CPC . G06T 7/0012; G06T 7/11; G06T 7/60; G06T 2207/20021; G06T 2207/30024;
(Continued)

(56) References Cited

U.S. PATENT DOCUMENTS

2010/0150423 A1   6/2010  Hong et al.
2010/0169811 A1*  7/2010  Yamada ............. G01N 15/1475
                                                     715/764

(Continued)

FOREIGN PATENT DOCUMENTS

EP    2833123 A1      2/2015
JP    2000-321031 A   11/2000
(Continued)

OTHER PUBLICATIONS

Preliminary Report on Patentability and Written Opinion which issued in the corresponding International Patent Application No. PCT/JP2016/053615.

(Continued)

*Primary Examiner* — Andrew W Johns
(74) *Attorney, Agent, or Firm* — Cozen O'Connor

(57) ABSTRACT

An image processing device prepares an interest image from an image obtained by photographing a cell in a sample and includes a cell image inputting unit, a setting unit, a preparation unit, and a display. The image is input to the image inputting unit. The setting unit sets one or more target images in the image. The preparation unit prepares plural candidate images by performing image processing of each of the one or more target images using one or more prescribed parameters. The display displays the plural candidate images prepared by the preparation unit.

14 Claims, 9 Drawing Sheets

(51) Int. Cl.
*G01N 33/48* (2006.01)
*G06T 1/00* (2006.01)
*G06T 7/60* (2017.01)
*G06T 7/11* (2017.01)
*G06T 7/136* (2017.01)

(52) U.S. Cl.
CPC ............. *G06T 1/00* (2013.01); *G06T 7/00* (2013.01); *G06T 7/0012* (2013.01); *G06T 7/11* (2017.01); *G06T 7/136* (2017.01); *G06T 7/60* (2013.01); *G06T 2207/20036* (2013.01); *G06T 2207/20092* (2013.01); *G06T 2207/30024* (2013.01); *G06T 2207/30096* (2013.01)

(58) Field of Classification Search
CPC .......... G01N 21/6447; G01N 21/6456; G01N 21/6458; G01N 21/6486
See application file for complete search history.

(56) References Cited

U.S. PATENT DOCUMENTS

| | | | |
|---|---|---|---|
| 2013/0016885 A1 | 1/2013 | Tsujimoto | |
| 2013/0301900 A1 | 11/2013 | Kiyuna et al. | |
| 2015/0138334 A1* | 5/2015 | Usuba et al. | G02B 21/365 348/79 |
| 2015/0356731 A1* | 12/2015 | Ozaki et al. | G01N 15/1475 382/134 |
| 2016/0004932 A1* | 1/2016 | Sano et al. | G06F 19/321 382/128 |

FOREIGN PATENT DOCUMENTS

| | | |
|---|---|---|
| JP | 2003-284705 A | 10/2003 |
| JP | 2006-079196 A | 3/2006 |
| JP | 2008-527546 A | 7/2008 |
| JP | 2012-255808 A | 12/2012 |
| JP | 2013-020212 A | 1/2013 |
| WO | WO 2006/047502 A2 | 5/2006 |
| WO | WO 2014/144657 A2 | 9/2014 |

OTHER PUBLICATIONS

Search Report dated Oct. 25, 2017 which issued in the corresponding European Patent Application No. 16755190.2.

* cited by examiner

IMAGE PROCESSING DEVICE, IMAGE PROCESSING METHOD, AND RECORDING MEDIUM STORING COMPUTER READABLE IMAGE PROCESSING PROGRAM

RELATED APPLICATIONS

This is a U.S. National Phase Application under 35 USC 371 of International Application PCT/JP2016/053615 filed on Feb. 8, 2016.

This application claims the priority of Japanese application no. 2015-032538 filed Feb. 23, 2015, the entire content of which is hereby incorporated by reference.

TECHNOLOGICAL FIELD

The present invention relates to an image processing device, an image processing method, and an image processing program, and specifically relates to image processing for pathological diagnosis.

BACKGROUND ART

A diagnosis of the presence of a lesion or the kind of the lesion, so called a pathological diagnosis, has been actively performed by observing a tissue slice obtained from a human or an animal with a microscope. In the pathological diagnosis, the obtained tissue sample is subjected to dehydration process for fixation, blocking process with paraffin, slicing process to cut the tissue sample into thin slices having a thickness of 2 to 8 µm, removing process of the paraffin, staining process, and observation process with a microscope to obtain image data (cell image). The diagnosis is includes analysis of change in size and shape of a cell nucleus, morphological information such as tissue pattern change, and staining information. When extraction of region of interest (for example, cell region) from a cell image is performed manually in the image processing, it takes a lot of time and causes large errors due to the difference of the operator, for example.

Recently, many techniques of automatic image analysis are suggested for the purpose of grasping cancer region efficiently, in which a specific protein is overexpressed, from an image of the tissue slice. For example, according to one of the suggested techniques, outline of individual cells are automatically extracted even when plural cells overlap in an image of a sample.

For example, according to the technique described in Patent Document 1, the shapes of individual cells can be extracted even when plural cells overlap with each other in the cell image (see paragraph 0018). In this technique, specifically by focusing on the dyeing concentration (concentration gradient) of cells, the shapes of individual cells are intended to be extracted on the basis of positive or negative codes of an inner product value of a concentration gradient vector at a pixel constituting the outline of a cell and a displacement vector from the pixel to the center of the cell (see paragraphs 0027 to 0028, FIG. 10, paragraphs 0084 to 0088, FIGS. 13 to 16, and the like).

According to the technique described in Patent Document 2, a constriction of the outline of overlapping plural cells is recognized as a boundary of individual cells using Watershed method, and each of the regions divided by the boundary is detected as a single cell.

According to the technique described in Patent Document 3, the region of interest in an image is automatically recognized by evaluating attribute values of each pixel in the image on the basis of feature amount of the observation target in a cell.

PRIOR ART DOCUMENT

Patent Document

Patent Document 1: Japanese Patent Application Laid-Open Publication No. 2000-321031
Patent Document 2: Japanese Patent Application Laid-Open Publication No. 2006-079196
Patent Document 3: Japanese Patent Application Laid-Open Publication No. 2008-527546

SUMMARY

Problems to be Solved by the Invention

As a matter of fact, in an image obtained by photographing cells, feature amounts of cells are often different according to the condition or the kind of the cells. Accordingly, it is necessary to adjust parameter values in image processing for each cell, in order to extract cell regions with high accuracy for all cells in the image. However, because it is difficult to perform automatic image processing including extraction of cell regions with high accuracy by adjusting parameters and the like for each cell, a user needs to modify the automatically extracted cell regions in part. Furthermore, when a fluorescent image which represents expression of a biological substance stained with a fluorescent substance is prepared, for example, it is difficult to perform automatic removal of noises due to contamination by foreign substances and the user needs to modify the fluorescent image in part. However, there is a problem that it takes time to manually and efficiently modify a part of the image.

A main object of the present invention is to provide an image processing device, an image processing method, and an image processing program which enable the user to easily modify a part of an image prepared by automatic image processing.

Means for Solving the Problem

To achieve at least one of the abovementioned objects, according to an aspect of the present invention, there is provided an image processing device which prepares an interest image from an image obtained by photographing a cell in a sample, the image processing device including:
a cell image inputting unit to which the image is input;
a setting unit which sets one or more target images in the image;
a preparation unit which prepares plural candidate images by performing image processing of each of the one or more target images using one or more prescribed parameters; and
a display which displays the plural candidate images prepared by the preparation unit.

To achieve at least one of the abovementioned objects, according to another aspect of the present invention, there is provided an image processing method which prepares an interest image from an image obtained by photographing a cell in a sample, the method including:
inputting the image of the cell;
setting one or more target images in the image;
preparing plural candidate images by performing image processing of each of the one or more target images using one or more prescribed parameters; and displaying the plural candidate images prepared in the preparing.

To achieve at least one of the abovementioned objects, according to another aspect of the present invention, there is provided an image processing program causing a computer which prepares an interest image from an image obtained by photographing a cell in a sample, to function as:

a cell image inputting unit to which the image is input;

a setting unit which sets one or more target images in the image;

a preparation unit which prepares plural candidate images by performing image processing of each of the one or more target images using one or more prescribed parameters; and a display unit which displays the plural candidate images prepared by the preparation unit.

Advantageous Effects of Invention

According to the present invention, provided are an image processing device, an image processing method, and an image processing program which enable a user to easily modify a part of an image prepared by automatic image processing.

The advantages and features provided by one or more embodiments of the invention will become more fully understood from the detailed description given hereinbelow and the appended drawings which are given by way of illustration only, and thus are not intended as a definition of the limits of the present invention.

Hereinafter, one or more embodiments of the present invention will be described with reference to the drawings. However, the scope of the invention is not limited to the disclosed embodiments.

Hereinafter, preferred embodiments of the present invention are described with reference to the drawings.

<Configuration of Pathological Diagnosis Assistance System 10>

Figure 1:
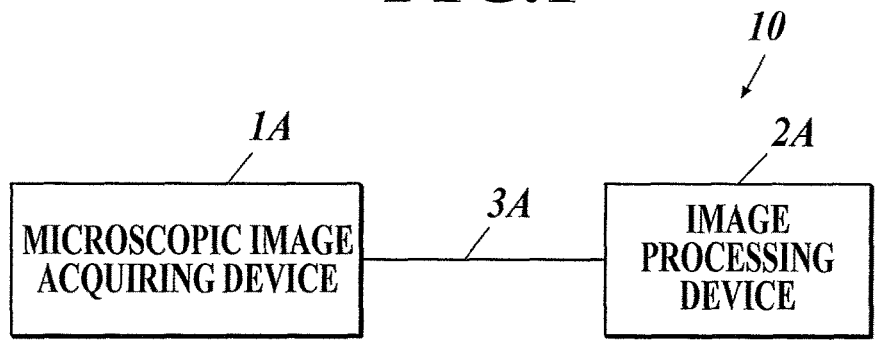
FIG. 1 is a diagram schematically showing a configuration of a pathological diagnosis assistance system.

FIG. 1 shows an exemplary entire configuration of a pathological diagnosis assistance system 10 including an image processing device according to the present invention.

The pathological diagnostic assistance system 10 obtains a microscopic image of a tissue slice of a human body stained with a prescribed staining reagent and outputs feature amount which represents an expression of a specific biological substance in the tissue slice of the observation target by analyzing the obtained microscopic image.

As shown in FIG. 1, the pathological diagnosis assistance system 10 includes a microscopic image obtaining apparatus 1A and an image processing device 2A connected to each other through an interface such as a cable 3A so as to be able to transmit and receive data.

The connecting system of the microscopic image obtaining apparatus 1A and the image processing device 2A is not particularly limited. For example, the microscopic image obtaining apparatus 1A and the image processing device 2A can be connected by a LAN (Local Area Network) or can be connected wirelessly.

The microscopic image obtaining apparatus 1A is a publically-known optical microscope with camera. The microscopic image obtaining apparatus 1A obtains the microscopic image of the tissue slice placed on the slide on a slide fixing stage, and transmits the image to the image processing device 2A.

The microscopic image obtaining apparatus 1A includes an irradiating unit, an image forming unit, a photographing unit, a communication I/F, etc. The irradiating unit includes a light source, filter, etc., and irradiates the tissue slice placed on the slide on the slide fixing stage with light. The image forming unit includes an ocular lens, an object lens, etc., and forms an image of transmitted light, reflected light, or fluorescence from the tissue slice on the slide due to the irradiated light. The photographing unit is a camera provided in a microscope which includes a CCD (Charge Coupled Device) sensor, etc., and photographs an image formed on an image forming face by the image forming unit to generate digital image data of the microscopic image. The communication I/F transmits the generated image data of the microscopic image to the image processing device 2A.

The microscopic image obtaining apparatus 1A includes a bright field unit combining an irradiating unit and an image forming unit suitable for bright field observation and a fluorescent unit combining an irradiating unit and an image forming unit suitable for fluorescent observation. The bright field observation and the fluorescent observation can be switched by changing the units.

The microscopic image obtaining apparatus 1A is not limited to a microscope with a camera. For example, a virtual microscope slide creating apparatus which scans a slide on a slide fixing stage of a microscope and obtains a microscopic image of the entire tissue slice can be used (for example, see Japanese Patent Application Laid-Open Publication No. 2002-514319). According to the image data obtained by the virtual microscope slide creating apparatus, the entire image of the tissue slice on the slide can be viewed at once on the display.

The image processing device 2A analyzes the microscopic image transmitted from the microscopic image obtaining apparatus 1A and calculates distribution of a specific biological substance expressed in the tissue slice of the observation target.

Figure 2:
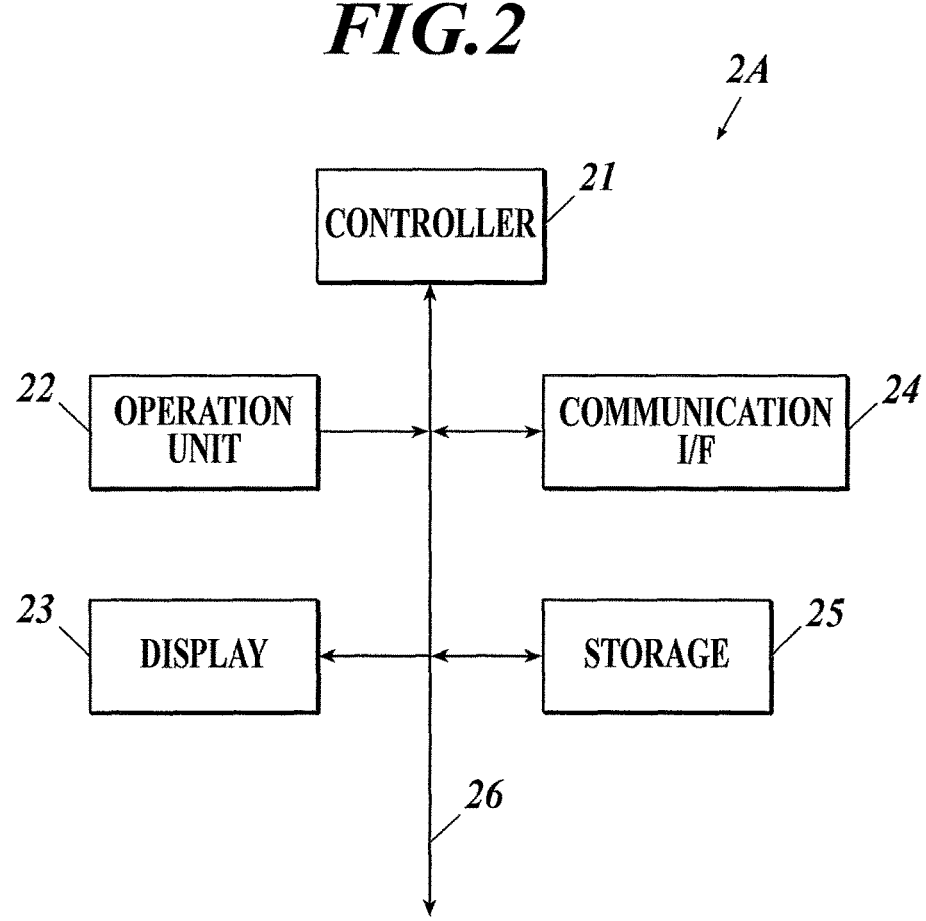
FIG. 2 is a block diagram schematically showing a functional configuration of an image processing device.

FIG. 2 shows an exemplary functional configuration of the image processing device 2A.

As shown in FIG. 2, the image processing device 2A includes a controller 21, an operation unit 22, a display 23, a communication I/F 24, a storage 25, and the like, and each section is connected through a bus 26.

The controller 21 includes a CPU (Central Processing Unit), a RAM (Random Access Memory), and the like, performs various processing in coordination with various programs stored in the storage 25, and collectively controls the operation of the image processing device 2A.

For example, the controller 21 performs image analysis processing (see FIG. 3) in coordination with an image processing program stored in the storage 25, and functions as a setting unit, a preparation unit, a selection unit, a determination unit, a judging unit, an evaluation unit, a display candidate image selection unit, a specification unit, and a fluorescent bright point extraction unit.

The operating unit 22 includes a keyboard provided with character input keys, numeric input keys, and various function keys and a pointing device such as a mouse or a stylus pen, and outputs depression signals of the pressed keys of the keyboard and operation signals of the mouse or the stylus pen as the input signal to the controller 21.

The display 23 includes a monitor such as a CRT (Cathode Ray Tube), an LCD (Liquid Crystal Display), etc., and functions as a display unit for displaying various screens according to an instruction of a display signal input from the controller 21.

The communication I/F 24 is an interface for transmitting and receiving data with external devices such as the microscopic image obtaining apparatus 1A. The communication I/F 24 functions as the cell image inputting unit and the fluorescent image inputting unit.

The storage 25 includes, for example, an HDD (Hard Disk Drive), a nonvolatile semiconductor memory, etc. The storage 25 stores various programs and various pieces of data as described above.

Other than the above, the image processing device 2A can include a LAN adaptor, a router, etc., and can be connected to external devices through a communication network such as a LAN.

In the present embodiment, the image processing device 2A analyzes a bright field image and a fluorescent image transmitted from the microscopic image obtaining apparatus 1A.

A "bright field image" is a microscopic image obtained by forming and capturing an enlarged image of a tissue slice stained with a reagent such as a hematoxylin staining reagent (H staining reagent) or a hematoxylin-eosin staining reagent (HE staining reagent) in a bright field in the microscopic image obtaining apparatus 1A. The bright field image is a cell morphology image showing shapes of cells in the tissue slice. Hematoxylin (H) is a blue purple dye and stains the cell nucleus, bone tissue, a portion of cartilage tissue, serous fluid component etc. (basophilic tissue, etc.). Eosin (E) is a red to pink dye and stains cytoplasm, connective tissue of soft tissue, red blood cell, fibrin, endocrine granule, etc. (eosinophilic tissue, etc.).

A "fluorescent image" is a microscopic image obtained as follows. A tissue slice is stained with a fluorescent staining reagent. The tissue sample is irradiated with an excitation light having a predetermined wavelength in the microscopic image acquiring device 1A so that a fluorescent light is emitted. The fluorescent light is enlarged, focused, and photographed.

A "fluorescent staining reagent" is a staining reagent including a fluorescent substance containing nanoparticle binding to a biological substance-recognizing site which specifically binds or reacts with a specific biological substance. A "fluorescent substance containing nanoparticle" (hereinafter may be referred to as a fluorescent particle) is a nanoparticle containing a fluorescent substance.

The fluorescence in the fluorescent image is emitted by excitation of the fluorescent substance containing nanoparticle (fluorescent substance) in the fluorescent staining reagent. The fluorescence represents expression of the specific biological substance in the tissue slice corresponding to the biological substance-recognizing site <Fluorescent Staining Reagent and Staining Method>

A fluorescent staining reagent and a staining method of a tissue slice using the fluorescent staining reagent will now be described.

(1) Fluorescent Substance

As for the fluorescent substance used as the fluorescent staining reagent, an organic fluorescent dye and a quantum dot (semiconductor particle) can be given as examples. The fluorescent substance preferably emit visual to near-infrared light having a wavelength in the range of 400 to 1100 nm when excited by ultraviolet to near-infrared light having a wavelength in the range of 200 to 700 nm.

As for the organic fluorescent dye, fluorescein dye molecules, rhodamine dye molecules, Alexa Fluor (manufactured by Invitrogen Corporation) dye molecules, BODIPY (manufactured by Invitrogen Corporation) dye molecules, cascade dye molecules, coumarin dye molecules, eosin dye molecules, NBD dye molecules, pyrene dye molecules, Texas Red dye molecules, cyanine dye molecules, and the like can be given as the example.

Specific examples of the dye may be 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine; Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, and BODIPY 650/665 (these are manufactured by Invitrogen Corporation); methoxycoumarin, eosin, NBD, pyrene, Cy5, Cy5.5, Cy7, and the like. These dyes may be used alone or in combination of two or more.

As for the quantum dot, quantum dots containing a II-VI group compound, a III-V group compound, or a IV group element as a component (also referred to as "II-VI group quantum dot", "III-V group quantum dot", and "IV group quantum dot", respectively) can be used. These quantum dots may be used alone or in combination of two or more.

Specific examples of the quantum dots may be, but are not limited to, CdSe, CdS, CdTe, ZnSe, ZnS, ZnTe, InP, InN, InAs, InGaP, GaP, GaAs, Si, and Ge.

A quantum dot constituted by the above-mentioned quantum dot as a core and a shell covering the core can also be used. Hereinafter, throughout the description, the quantum dot having a shell is represented by, for example, CdSe/ZnS for a combination of a CdSe core and a ZnS shell.

For example, CdSe/ZnS, CdS/ZnS, InP/ZnS, InGaP/ZnS, Si/SiO$_2$, Si/ZnS, Ge/GeO$_2$, or Ge/ZnS can be used, but the quantum dot is not limited thereto.

The quantum dot whose surface is modified with an organic polymer or the like may be used, if necessary. For example, CdSe/ZnS having carboxy groups on the surface (manufactured by Invitrogen Corporation) and CdSe/ZnS having amino groups on the surface (manufactured by Invitrogen Corporation) can be given as examples.

(2) Fluorescent Substance Containing Nanoparticle

A "fluorescent substance containing nanoparticle" is a nanoparticle containing a fluorescent substance as described above, and specifically refers to a nanoparticle in which fluorescent substance is dispersed. The fluorescent substance may chemically bind to the nanoparticle itself or not.

The nanoparticle may be composed of any material without particular limitation, and silica, polystyrene, polylactic acid, and melamine can be given as examples.

The fluorescent substance containing nanoparticle can be prepared by known method.

For example, an organic fluorescent dye-containing silica nanoparticle can be synthesized with reference to the synthesis of FITC-containing silica particle described in Langmuir, vol. 8, p. 2921, (1992). Various organic fluorescent dye-containing silica particles can be synthesized with a desired organic fluorescent dye instead of FITC.

A quantum dot-containing silica nanoparticle can be synthesized with reference to the synthesis of CdTe-containing silica nanoparticle described in New Journal of Chemistry, vol. 33, p. 561, (2009).

An organic fluorescent dye-containing polystyrene nanoparticle can be prepared by copolymerization of an organic dye having a polymerizable functional group described in U.S. Pat. No. 4,326,008 (1982) or impregnation of a polystyrene nanoparticle with an organic fluorescent dye described in U.S. Pat. No. 5,326,692 (1992).

A quantum dot-containing polymer nanoparticle can be prepared by impregnation of a polystyrene nanoparticle with quantum dot described in Nature Biotechnology, vol. 19, p. 631, (2001).

The average particle diameter of the fluorescent substance containing nanoparticle is not particularly limited, but is preferably about 30 to 800 nm. The coefficient of variation (=(standard deviation/average value)×100%), which shows a distribution in particle diameter, is not particularly limited, but is preferably 20% or less.

The average particle diameter is determined by taking an electron micrograph with a scanning electron microscope (SEM), measuring cross-sectional areas of a sufficient number of the particle, and using the diameters of circles each having the same area as each of the measured cross-sectional areas. In the present embodiment, the arithmetic average of particle diameters of 1000 particles is determined as the average particle diameter. The coefficient of variation is also calculated based on the particle size distribution of 1000 particles.

(3) Binding of Biological Substance-Recognizing Site to Fluorescent Substance Containing Nanoparticle The "biological substance-recognizing site" according to the present invention is a site which specifically binds to and/or reacts with a specific biological substance.

The specific biological substance is not particularly limited, as long as there is a substance which specifically binds to the specific biological substance. Typical example of the specific biological substance includes a protein (peptide), nucleic acid (oligonucleotide and polynucleotide), and the like.

Accordingly, exemplary biological substance-recognizing site may be an antibody which recognizes the protein as an antigen, another protein which specifically binds to the antibody, or a nucleic acid having a base sequence which can hybridize to the above-described nucleic acid.

Specific examples of the biological substance-recognizing site can be an anti-HER2 antibody which specifically binds to HER2, which is a protein present on cell surface; an anti-ER antibody which specifically binds to an estrogen receptor (ER), which is present on cell nuclei; anti-actin antibody which specifically binds to actin, which forms cytoskeletons; and the like.

In particular, a fluorescent substance-containing nanoparticle to which the anti-HER2 antibody or the anti-ER antibody binds is suitable, because such nanoparticle can be used for selecting a drug for breast cancer.

Biological substance-recognizing site may bind to the fluorescent substance containing nanoparticle in any form without particular limitation, and covalent bonding, ion bonding, hydrogen bonding, coordinate bonding, physisorption, and chemisorption can be given as examples. From the point of stability of binding, bonding having a strong binding force, such as covalent bonding, is suitable.

Furthermore, any organic molecule for linking the biological substance-recognizing site and the fluorescent substance containing nanoparticle may be used. For example, in order to inhibit non-specific adsorption to a biological substance, a polyethylene glycol chain can be used, and SM(PEG)12 manufactured by Thermo Scientific Inc. can be used.

In binding the biological substance-recognizing site to the fluorescent substance containing nanoparticle, the same procedure can be used in all cases of using an organic fluorescent dye or quantum dot as the fluorescent substance.

For example, a silane coupling agent, which is a compound widely used for binding an inorganic material with an organic material, can be used. The silane coupling agent is a compound having an alkoxysilyl group which gives a silanol group through hydrosis at one end of the molecule and a functional group at the other end, such as a carboxyl group, an amino group, an epoxy group, or an aldehyde group. The silane coupling agent binds to an inorganic material via the oxygen atom of the silanol group.

Specifically, mercaptopropyltriethoxysilane, glycidoxypropyltriethoxysilane, aminopropyltriethoxysilane, silane coupling agents having polyethylene glycol chains (e.g., PEG-silane no. SIM6492.7 manufactured by Gelest Inc.), and the like are given as examples of the silane coupling agent.

When the silane coupling agents is used, two or more types thereof can be used in combination.

The reaction procedure of the silane coupling agent with organic fluorescent dye-containing silica nanoparticle may be performed by any known method.

For example, the prepared organic fluorescent dye-containing silica nanoparticle is dispersed in pure water, and then aminopropyltriethoxysilane is added thereto for a reaction at room temperature for 12 hours. After completion of the reaction, centrifugation or filtration is performed to obtain an organic fluorescent dye-containing silica nanoparticle having a surface modified with aminopropyl groups.

Subsequently, the amino group is made to react with a carboxyl group of an antibody to bind the antibody to the organic fluorescent dye-containing silica nanoparticle via an amide bond. Furthermore, a condensing agent such as 1-ethyl-3-[3-dimethylaminopropyl]carbodiimide hydrochloride (EDC, manufactured by Pierce) may be used as needed.

A linker compound having a site that can directly bind to an organic fluorescent dye-containing silica nanoparticle modified with an organic molecule and a site that can bind to a molecular target material can be used as needed. Specifically, by using sulfosuccinimidyl 4-[N-maleimidomethyl]-cyclohexane-1-carboxylate (sulfo-SMCC, manufactured by Pierce) having a site which selectively reacts with an amino group and a site which selectively reacts with a mercapto group, the amino group of an organic fluorescent dye-containing silica nanoparticle modified with aminopropyltriethoxysilane binds to the mercapto group of an antibody to provide an organic fluorescent dye-containing silica nanoparticle to which the antibody binds.

Binding of a biological substance-recognizing site to a fluorescent substance-containing polystyrene nanoparticle can be achieved by substantially the same procedure in all cases of using an organic fluorescent dye and a quantum dot as the fluorescent substance. That is, a polystyrene nanoparticle having a functional group such as an amino group is impregnated with an organic fluorescent dye or quantum dots to provide a fluorescent substance-containing polystyrene particle having a functional group. A subsequent use of EDC or sulfo-SMCC can provide a fluorescent substance-containing polystyrene nanoparticle to which an antibody binds.

Example of the biological substance-recognizing site includes the following antibodies, which recognize a specific antigen: M. actin, M.S. actin, S.M. actin, ACTH, Alk-1, .alpha.1-antichymotrypsin, .alpha.1-antitrypsin, AFP, bcl-2, bcl-6, .beta.-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, C-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, *Helicobacter pyroli*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, p63, PAX 5, PLAP, *Pneumocystis calini*, podoplanin (D2-40), PGR, prolactin, PSA, prostatic acid phosphatase, Renal Cell Carcinoma, 5100, somatostatin, spectrin, synaptophysin, TAG-72, TdT, cycloglobulin, TSH, TTF-1, TRAcP, tryptase, villin, vimentin, WT1, Zap-70, and the like.

(4) Staining Method

The staining method described below is not limited to a pathological tissue slice, and can be applied to cultured cells.

The method of preparing a tissue slice is not particularly limited, and slices prepared by a known method can be used.

(4.1) Removing Paraffin

A tissue slice is immersed in xylene in a container to remove paraffin. The immersion may be performed at any temperature without particular limitation, for example, at room temperature. The immersion time is preferably 3 minutes or more and 30 minutes or less. The xylene may be replaced with new xylene during the immersion if necessary.

Subsequently, the tissue slice is immersed in ethanol in a container to remove the xylene. The immersion may be performed at any temperature without particular limitation, for example, at room temperature. The immersion time is preferably 3 minutes or more and 30 minutes or less. The ethanol may be replaced with new ethanol during the immersion if necessary.

Subsequently, the tissue slice is immersed in water in a container to remove the ethanol. The immersion may be performed at any temperature without particular limitation, for example, at room temperature. The immersion time is preferably 3 minutes or more and 30 minutes or less. The water may be replaced with new water during the immersion if necessary.

(4.2) Retrieval Process

In accordance with a known method, the biological substance in the tissue slice is subjected to retrieval process.

The retrieval process can be performed under any condition without limitation. As for a retrieving solution, a 0.01 M citrate buffer solution (pH 6.0), a 1 mM EDTA solution (pH 8.0), 5% urea, a 0.1 M Tris-hydrochloride buffer solution, or the like can be used. As for a heater, an autoclave, a microwave heater, a pressure cooker, a water bath, or the like can be used. The activation may be performed at any temperature without particular limitation, for example, at room temperature. The temperature may range from 50 to 130° C., and the time may range from 5 to 30 minutes.

Subsequently, the slice after the retrieval process is washed by being immersed in water and PBS (Phosphate Buffered Saline) in containers. The washing may be performed at any temperature without particular limitation, for example, at room temperature. Each immersion time is preferably 3 minutes or more and 30 minutes or less. The PBS may be replaced with new PBS during the immersion if necessary.

(4.3) Staining with Fluorescent Staining Reagent

The PBS dispersion liquid of the fluorescent staining reagent is placed on the tissue slice and reacted with the target biological substance in the tissue slice.

By changing the biological substance-recognizing site binding to the fluorescent substance containing nanoparticle, staining can be applied to various biological substances. When the fluorescent substance containing nanoparticle binds to plural types of biological substance-recognizing sites, the PBS dispersion liquid of each fluorescent substance containing nanoparticle may be mixed in advance, or each liquid may be placed on the pathological slice separately and sequentially. The temperature is not limited, and the process can be performed at room temperature. Preferably, the reacting time is 30 minutes or more and 24 hours or less.

Preferably, a known blocking agent such as BSA-including PBS is dropped before staining with the fluorescent staining reagent.

Next, the tissue slice after staining is immersed in the container with PBS, and the unreacted fluorescent substance containing nanoparticle is removed. The temperature is not limited, and the process can be performed at room temperature. Preferably, the immersing time is 3 minutes or more and 30 minutes or less. The PBS may be replaced with new PBS during the immersion if necessary. A cover glass is placed on the slice to be sealed. A commercially available sealing agent can be used if necessary.

HE staining is performed before sealing with the cover glass using a HE stainig reagent.

(5) Obtaining Fluorescent Image

The microscopic image obtaining apparatus 1A is used on the stained tissue slice to obtain the microscopic image (fluorescent image) with a wide field. In the microscopic image obtaining apparatus 1A, the excitation light source and the fluorescence detecting optical filter are selected corresponding to the absorption maximum wavelength and the fluorescent wavelength of the fluorescent substance used in the staining reagent.

Preferably, the field of the fluorescent image is 3 mm$^2$ or more, more preferably 30 mm$^2$ or more, and even more preferably 300 mm$^2$ or more.

<Operation of Pathological Diagnosis Assistance System 10 (Including Image Processing Method)>

Hereinafter, the operation of preparing an interest image from the above described bright field image and fluorescent image according to the image processing method of the present invention is described, including the step of preparing pathological diagnosis information in the pathological diagnosis assistance system 10. Here, the observation target is a tissue slice of a breast cancer in which HER2 protein is stained as a specific protein, and the interest image is an image in which a cell region(s) is extracted as a region(s) of interest.

EXAMPLE

First, the operator stains a tissue slice using two kinds of staining reagent, i.e., an HE staining reagent and a fluorescent staining reagent (a fluorescent substance-containing nanoparticle with anti HER2 antibody bonded).

Subsequently, a bright field image and a fluorescent image are obtained with the microscopic image obtaining apparatus 1A by the procedures of (a1) to (a5).

(a1) The operator mounts the tissue slice stained by an HE staining reagent and a fluorescent staining reagent on a slide, and places the slide on a slide fixing stage of the microscopic image obtaining apparatus 1A.

(a2) The bright field unit is set, the capturing magnification and focus are adjusted, and the region of the observation target of the tissue slice is put in the visual field.

(a3) Capturing is performed with the capturing unit to generate the image data of the bright field image, and the image data is transmitted to the image processing device 2A.

(a4) The unit is changed to the fluorescent unit.

(a5) Capturing is performed with the capturing unit without changing the visual field and the capturing magnification to generate the image data of the fluorescent image, and the image data is transmitted to the image processor 2A.

Subsequently, an image analysis processing is performed on the basis of the bright field image and the fluorescent image by the image processing device 2A.

Figure 3:
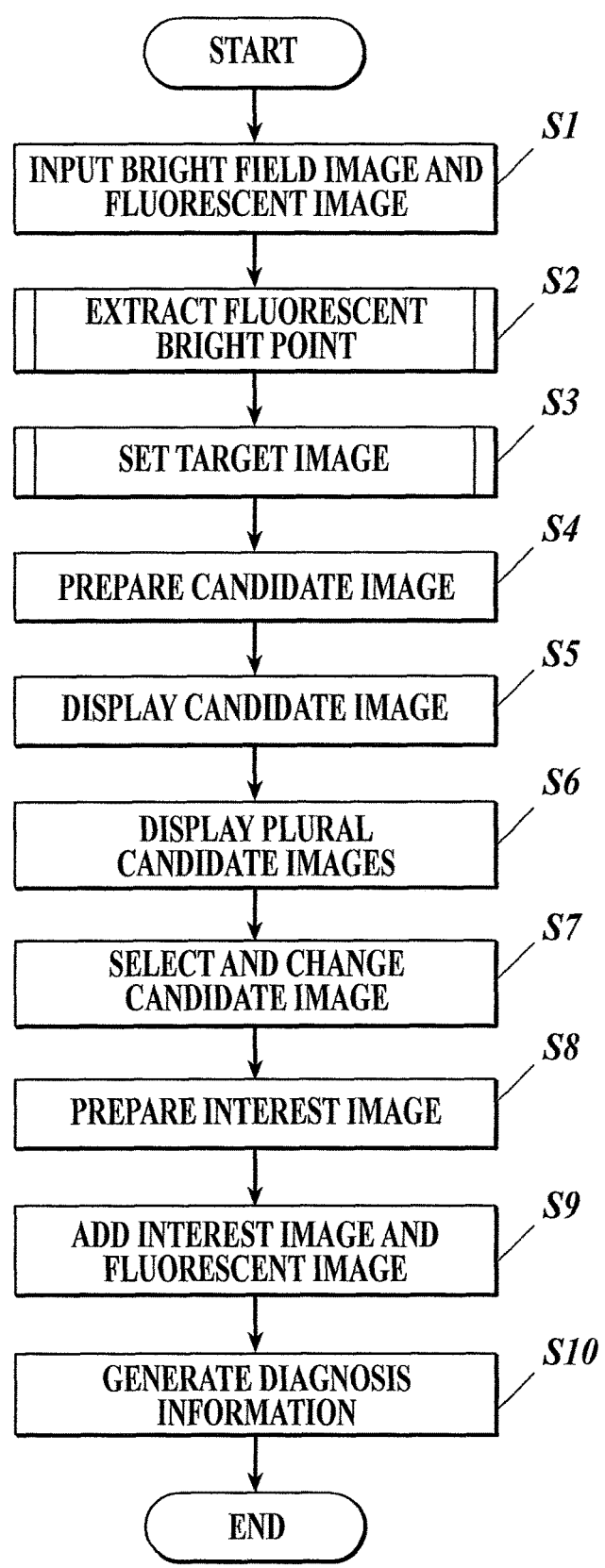
FIG. 3 is a flowchart schematically showing a flow of image processing in the EXAMPLE.

The flowchart of FIG. 3 shows the image analysis processing.

The image analysis processing shown in FIG. 3 is performed by the controller 21 in coordination with an image processing program stored in the storage 25. The controller 21 performs the processing described below in accordance with the image processing program.

When the bright field image and the fluorescent image are input from the microscopic image obtaining apparatus 1A through the communication I/F 24 (Step S1: step of inputting image, step of inputting fluorescent image), the controller 21 extracts fluorescent bright points from the fluorescent image (Step S2: a fluorescent bright point extraction step).

Figure 4:
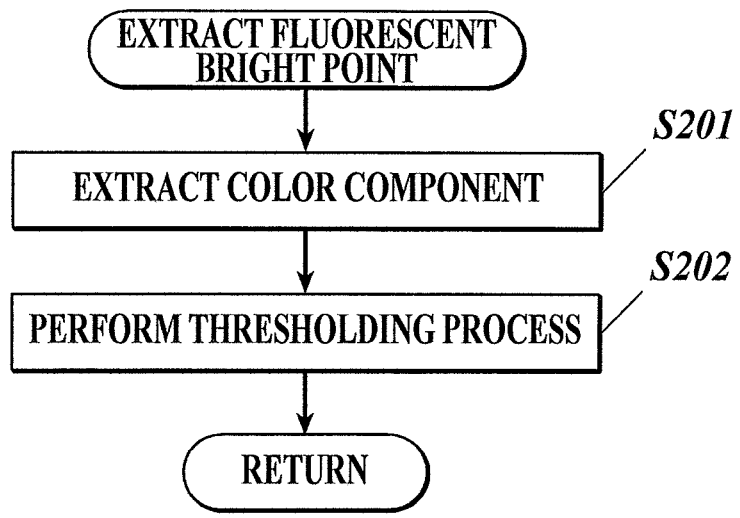
FIG. 4 is a flowchart schematically showing a flow of fluorescent bright point extraction.

In Step S2, as shown in FIG. 4, a color component is extracted from the fluorescent image according to the wavelength of the fluorescent bright points (Step S201). The fluorescent image after extracting the color component is subjected to a thresholding process to generate a binary image (Step S202). An image (fluorescent bright point image) is prepared through the Steps S201 to S202 by extracting fluorescent bright points from the fluorescent image.

In Step S201, for example, when the fluorescent particle emits light having a wavelength of 550 nm, only the fluorescent bright points having the wavelength of 550 nm is extracted to prepare the image. Before the thresholding process in step S202, a noise removal process may be executed to remove autofluorescent noise of cells and other unnecessary signals.

After the process of step S203, one or more target images are set in the bright field image to perform an image process for preparing an interest image (step S3: setting step). Any known method may be used for setting the target images. Preferably, each of the regions of interest (in the present embodiment, individual cells) is not set into separate target images in step S3, because the target images are respectively subjected to image processing for extracting the regions of interest after step S4. Therefore, it is preferred that plural candidates of the target image are prepared and that, among the plural candidates, the one having the maximum size is determined as the target image. Otherwise, a target image may be determined by, for example, a dilation process of a candidate of the target image set by any known image processing method. Any number of target images may be set in the bright field image.

Figure 5:
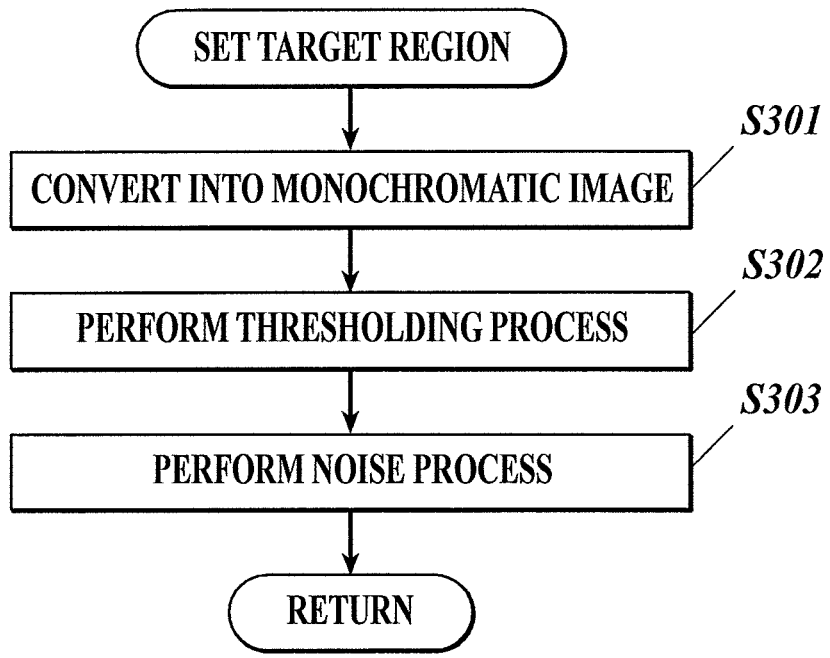
FIG. 5 is a flowchart schematically showing a flow of cell extraction.

The exemplary steps of setting target images (step S3) is illustrated in the flowchart of FIG. 5 in detail.

Figure 8A:
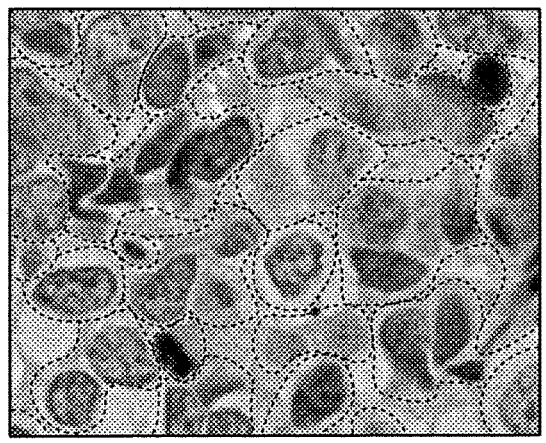
FIG. 8A is an exemplary bright field image.

The controller 21 converts the bright field image into a monochromatic image (step S301). The monochromatic image is then subjected to a thresholding process to binarize the each pixel value using a predetermined threshold (Step S302). Through the image processing such as noise reduction processing and dilation processing of the binary image, target images are set (step S303). FIG. 8A is an exemplary bright field image, in which the set target images are shown as the images surrounded by a dotted line.

Any threshold may be used in step S302. For example, the threshold may be adjusted so that the regions in the binary image are sufficiently larger than the actual cell and that the target images are set without a dilation process in step S303.

Specifically, noise removal process in step S303 can be performed by closing process of the binary image. The closing process includes dilation process and erosion process at the same number of times. In the dilation process, when any of the pixels within the range of n×n pixels (n is an integer of 2 or more) from the target pixel is white, the target pixel is replaced with a white pixel. In the erosion process, when any of the pixels within the range of n×n pixels from the target pixel is black, the target pixel is replaced with a black pixel. Small regions such as noise can be removed by the closing process.

In steps S301 to 303, target images including cells are set in the bright field image.

The process of steps S2 and S3 may be performed in reverse order.

Subsequently, the controller 21 prepares candidate images for each target image prepared in step S3 (step S4: preparing step). The candidate images may be prepared in any number, but preferably plural numbers, so that an image which is most likely to be the desired interest image can be selected.

The candidate images are prepared by any method, for example, by image processing based on luminance, chromaticity, or edge of the target image. In the image processing based on luminance, for example, the candidate images are prepared by calculating the luminance of each pixel within the target images in the bright field image and by a binarizing process using a threshold as a parameter. In the image processing based on chromaticity, for example, the candidate images are prepared by RGB separation of each pixel in the target images in the bright field image and by a binarizing process of a prescribed color component using a threshold as a parameter. In image processing based on edge, the candidate images are prepared by changing parameters used in the image processing of extracting cell edge.

Plural candidate images are prepared by changing the parameter values within a prescribed range in the above image processing. The range of the parameter value can be optionally set on the basis of the kind of tissue sample or the interest image, conditions in photographing the bright field image, and the like.

Subsequently, for each of the target images prepared in step S3, the controller 21 displays one of the candidate images (step S5).

Figure 8B:
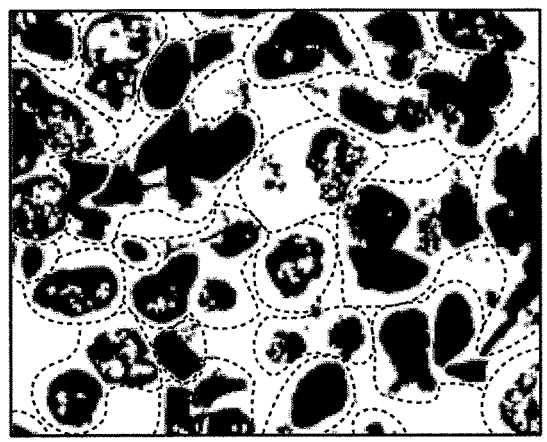
FIG. 8B is an exemplary binary image prepared from a bright field image.

FIG. 8B illustrates exemplary candidate images displayed in step S5, specifically, binary images prepared by performing the same image processing (an adjusting process of contrast and lightness and a binarizing process) for all target images of FIG. 8A. The candidate images may be displayed in an optional manner. For example, the bright field image and the candidate images can be easily compared when candidate images are binary images as in FIG. 8B, by superimposing and displaying the images after making the candidate image translucent at the parts other than the outline of the black region in the binary image.

Figure 6A:
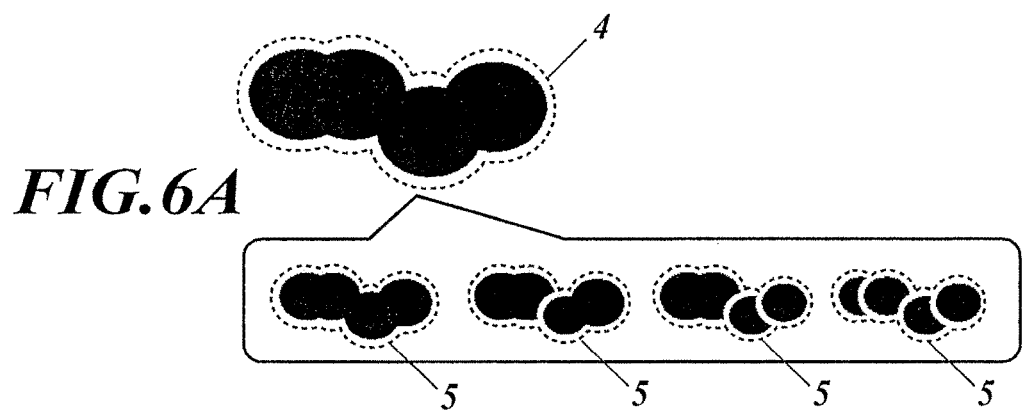
FIG. 6A is a schematic diagram illustrating an exemplary method for displaying candidate images.

Subsequently, when a user specifies the image to be corrected among the displayed candidate images via the operation unit 22, the controller 21 displays the plural candidate images prepared in step S4 on the display 23 (step S6: display step). The plural candidate images displayed in step S6 are prepared by image processing of the target image, from which the specified candidate image is prepared, using parameter values different from each other. FIG. 6A shows an exemplary candidate image 4 and exemplary plural candidate images 5 displayed in step S5. The plural candidate images 5 are prepared by image processing of cell edge extraction using different parameter values from each other.

Before or after the process of step S5, the controller 21 may perform the step of selecting plural candidate images to be displayed in step S6 from the candidate images prepared in step S4 (a display candidate image selection step). In the display candidate image selection step, according to the signal input by the user via the operation unit 22, for example, the controller 21 selects one or more candidate images which are processed using parameters within a prescribed range from the candidate images prepared in step S4. For example, FIG. 6A illustrates the plural candidate images 4 selected and displayed in step S6, which are subjected to edge extraction using parameter values so that the candidate image is further divided.

Figure 6B:
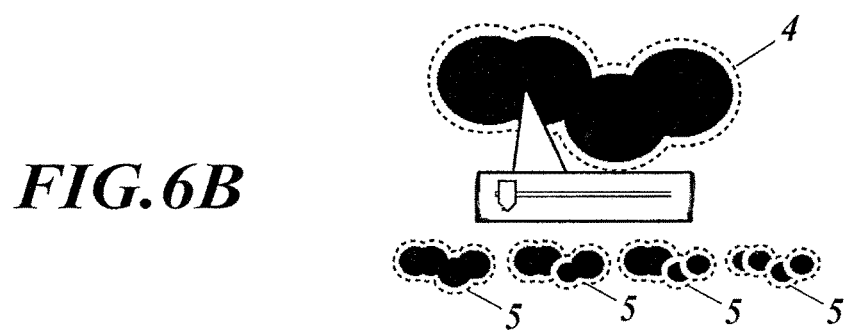
FIG. 6B is a schematic diagram illustrating an exemplary method for displaying candidate images.

When the user specifies one of the candidate images on the display via an operation with the operation unit 22, a slide bar may be displayed near the candidate image 4 as in FIG. 6B, for example, and the specified candidate image 4 may be replaced with one of the candidate images 5 according to the slider operation of the slide bar by the user. Specifically, the displayed candidate image 5 is prepared by an image processing of edge extraction using a parameter which continuously changes according to the position of the slider as shown in FIG. 6B.

The operation by the user is not limited to the slider operation of the slide bar but any known operation method, such as scrolling operation via a mouse and keyboard operation.

When the plural candidate images are displayed at the same time, the arrangement of the plural candidate images are preferably determined on the basis of the parameter value used in the image processing. For example, when the plural candidate images are displayed on a straight line as in FIG. 6A, it is preferred that the parameter used in the image processing of each candidate image 5 monotonically increases or monotonically decrease along the straight line. As a result, the user can easily compare the plural candidate images 5.

Figure 6C:
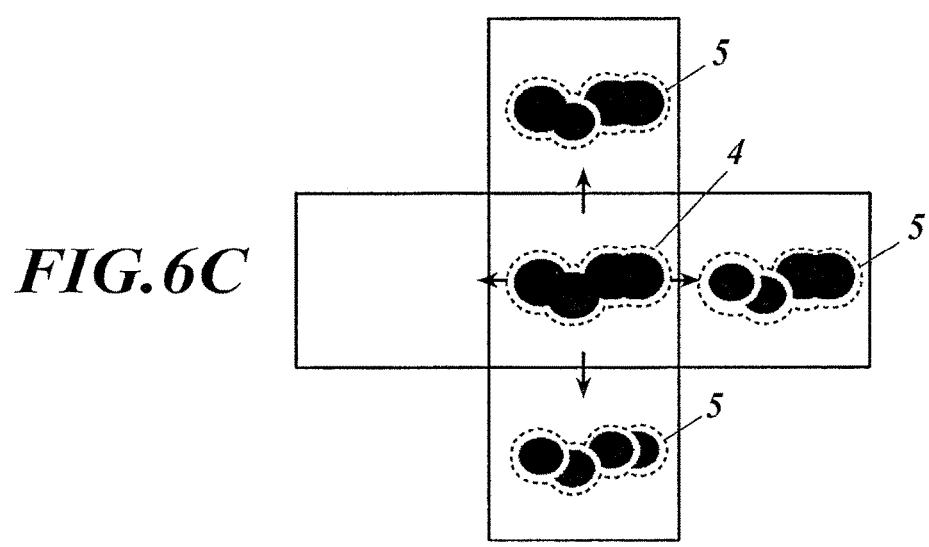
FIG. 6C is a schematic diagram illustrating an exemplary method for displaying candidate images.

The candidate images 5 may be displayed by any method, for example, as shown in FIG. 6C, the plural candidate images 5 may surround the candidate image 4 displayed in step S5. In this case, the plural candidate images 5 are preferably arranged and displayed so that the parameters used in the image processing monotonically increase or monotonically decrease in the clockwise or counterclockwise direction around the candidate image 4 displayed in step S5.

In step S6, the displayed plural candidate images may be different from each other not only in one kind of parameter in the image processing but also in plural kinds of parameters in the image processing.

Figure 7:
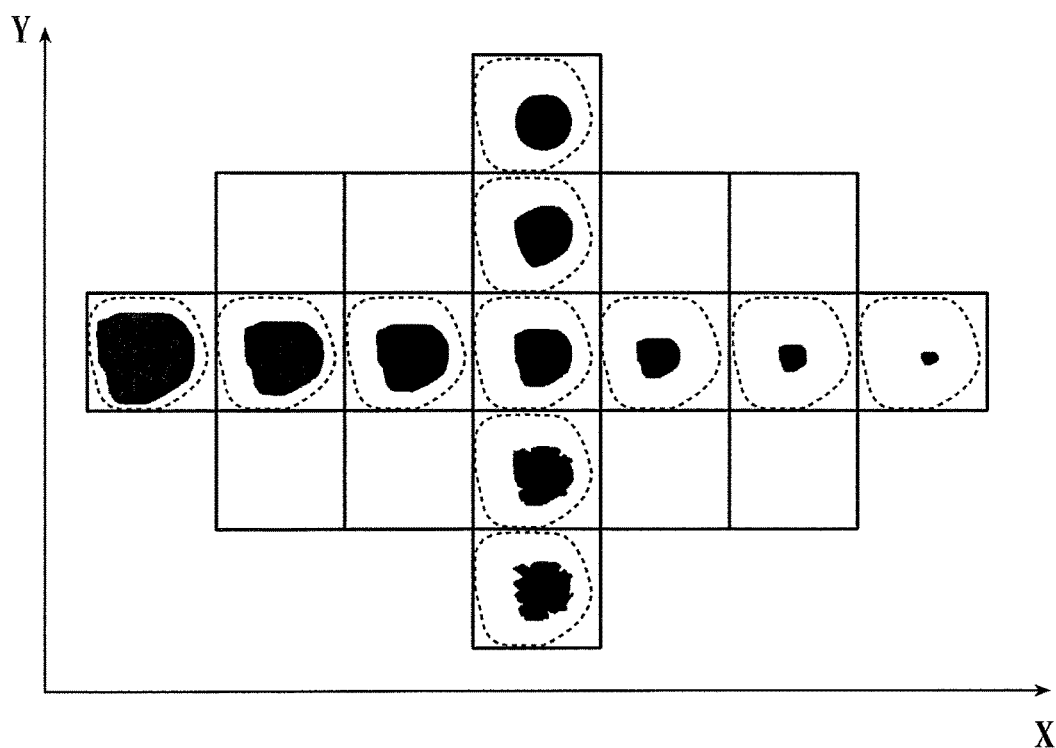
FIG. 7 is a schematic diagram illustrating an exemplary method for displaying candidate images.

FIG. 7 shows exemplary displayed candidate images processed using a parameter X to specify the degree of dilation and a parameter Y to specify circularity. In FIG. 7, the candidate images are displayed on a two-dimensional coordinate with a horizontal axis as the parameter X a vertical axis as the parameter Y. The position of the each candidate image in the two-dimensional coordinate corresponds to the parameter values for image processing.

In performing image processing using plural parameters, the plural candidate images may be displayed as follows; plural candidate images are prepared by changing the value of any one of the parameters and displayed as in FIG. 6A; the user selects one of the candidate images; and plural candidate images are further prepared by changing the value of another parameter for the selected candidate image and displayed.

Subsequently, in step S7, the user selects one of the candidate images 5 displayed in step S6 via the operation unit 22 (selection step). The controller then 21 replaces the candidate image 4 specified by the user in step S6 with the candidate image 5 selected by the user in step S7.

The user may select one of the candidate images 5 by any method. For example, when plural candidate images 5 are displayed as in FIG. 6A, the user may select one of the candidate images 5 via the operation unit 22 (for example, operation via a mouse or a stylus pen). In the case that the displayed candidate image 5 changes according to the slider operation of the slide bar as in FIG. 6B, for example, the user selects the candidate image 5 by performing a prescribed operation via the operation unit 22 (for example, a prescribed key operation or a prescribed operation via a mouse or a stylus pen) at the time when a desired candidate image 5 is displayed.

The user repeatedly performs the processing of Steps S6 to S7 for the candidate images to be changed. When it is decided that it is not necessary to change the displayed candidate image, the user inputs a determination signal via the operation unit 22. When the determination signal signal is input, the controller 1 determines that the displayed candidate images composes an interest image (step S8: determination step).

Figure 8C:
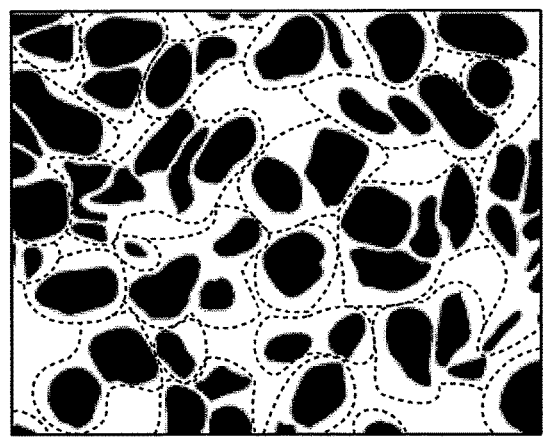
FIG. 8C is an exemplary interest image prepared by the method of the present invention.

FIG. 8C is an exemplary interest image prepared from the bright field image of FIG. 8A. The black regions are regions of interest.

Subsequently, addition process (step S9) of the interest image and the fluorescent bright point image is performed. On the basis of the superimposed images after the addition process, diagnosis information (for example, the density of the fluorescent bright points in the region of interest) is generated (step S10).

Preferably, the target images once specified can be replaced. For example, when the user operates a prescribed operation (for example, key operation of a keyboard) after step S6 or S7, the controller 21 resets the specification of target images and returns to the processing of step S3, so that target images can be specified again.

Modified Example 1

The controller 21 may judge whether or not there is a deviation in a prescribed feature amount distribution (judging step). When the deviation is less than a prescribed degree, the whole bright field image may be set to be one target image. According to the MODIFIED EXAMPLE 1, it is recognized that partial adjustment of a part of the image is not necessary when the feature amount is distributed without deviation in the whole bright field image. Therefore, the whole image is processed collectively as in the conventional image processing.

Any known feature amount of the bright field image may be used, for example, contrast, gradation value after gray scale conversion, average optical density, texture, and color.

The deviation of the feature amount distribution may be judged by any means. For example, when the pixel value of the bright field image after monochrome conversion is determined as the feature amount, the bright field image is divided into a prescribed number of sections and the averaged pixel value is calculated in each of the sections. When the standard deviation of the averaged pixel value is larger than a prescribed value, it is judged that there is a large sectional variation of pixel value, that is, there is a deviation of feature amount distribution.

Modified Example 2

The image processing device according to the present invention may have a specification unit to specify a candidate image group including grouped candidate images set in step S3 of the above EXAMPLE.

Figure 9:
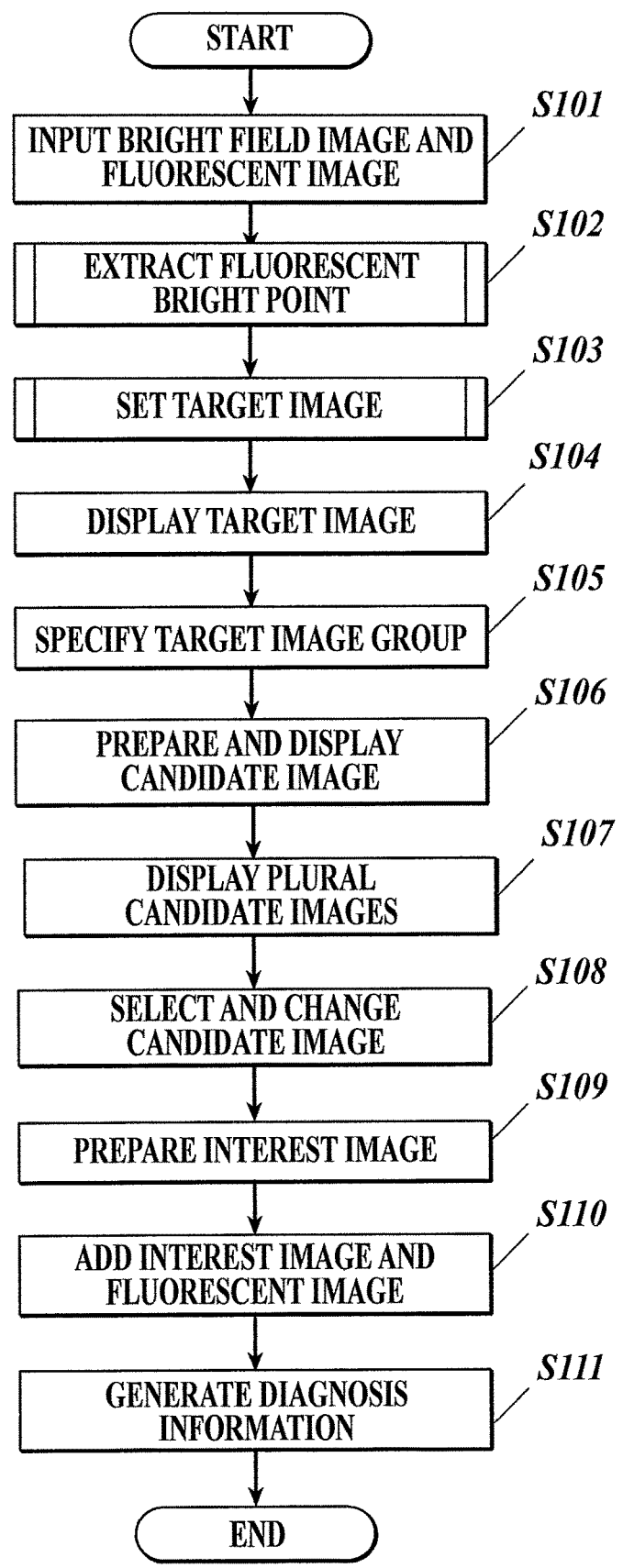
FIG. 9 is a flowchart schematically showing a flow of image processing in the MODIFIED EXAMPLE 2.

Hereinafter, the image processing of MODIFIED EXAMPLE 2 is specifically described on the basis of the flowchart in FIG. 9. The configurations different from those in the image processing of the above EXAMPLE are mainly explained and the configurations common to the EXAMPLE are omitted.

The processes in steps S101 to S103 in the MODIFIED EXAMPLE 2 are the same as those in steps S1 to S3 in the above EXAMPLE. Subsequently, the controller 21 displays the target images in the display 23 (step S104). Subsequently, the user optionally selects the target images displayed in step S104 via the operation unit 22 and specifies a target image group by grouping the target images (step S105: specification step).

The outlines of the target images are preferably displayed on the bright field image in step S104, for example. As a result, the whole bright field image and the target images can be easily compared and the target images having similar feature amount can be easily selected and grouped. In the specification step, the target images desired to be grouped may be specified by selecting the images one by one, or by surrounding the images via a mouse operation etc.

Any number of the target image groups may be specified in the bright field image. There may be some target image(s) which is not grouped.

Figure 10:
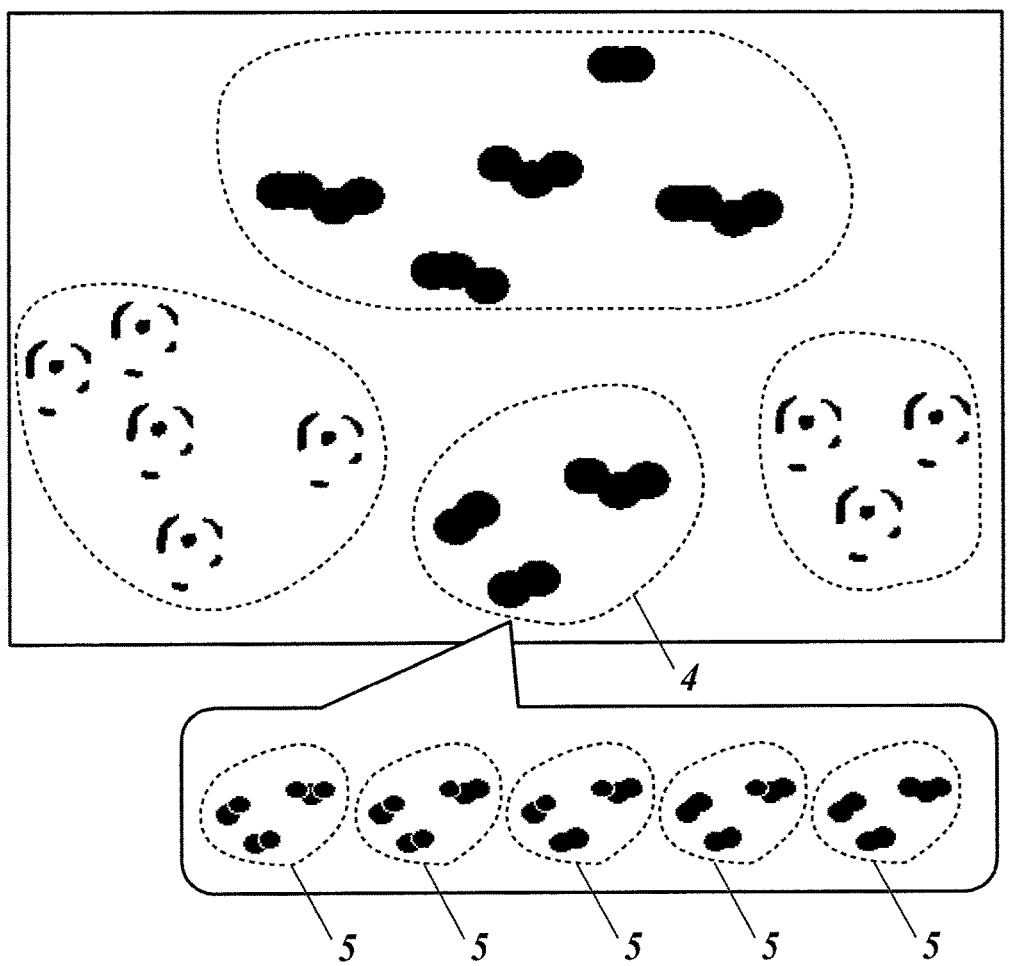
FIG. 10 is a schematic diagram illustrating an exemplary method for displaying candidate images in the MODIFIED EXAMPLE 2.

After specification of the target image group, the controller 21 prepares candidate images as in the steps S4 to S5 in the above EXAMPLE and displays one of the candidate image (step S106). In step S106, a candidate image is prepared and displayed by performing image processing collectively for the target images of the same candidate image group. FIG. 10 is a schematic diagram illustrating exemplary displayed candidate images (images surrounded by a dotted line) prepared for each target image group.

Subsequently, when the user specifies the image to be corrected from the displayed candidate images via an operation with the operation unit 22, plural candidate images are displayed (step S107) as in the step S6 of the above EXAMPLE. The schematic diagram in FIG. 10 illustrates exemplary plural candidate images 5 prepared from the candidate image 4 displayed in step S107.

Subsequently, in step S108 (selection step), the user selects one of the candidate images 5 displayed in step S107 via an operation with the operation unit 22. The controller 21 replaces the candidate image 4 specified by the user in step S107 with the candidate image 5 selected by the user in step S108.

The processes in steps S109 to S111 are the same as those in steps S8 to S10 in the above EXAMPLE.

According to the MODIFIED EXAMPLE 2, the target images having similar feature amount are grouped and specified as a target image group, and the image processing and the correction via the user operation can be performed not for each target image, but collectively for the target image group. As a result, there is an advantage that the time and cost of image processing are reduced.

The target image groups are set not only by the user operation in step S105. For example, the controller 21 calculates the feature amount of each target image set in step S103, and sets the images having similar feature amount as the same target image group. Any known feature amount of the target image may be used, for example, contrast, gradation value after gray scale conversion, average optical density, texture, and color.

The step of specifying target image groups is not performed only before preparation of the candidate image as illustrated in FIG. 10. For example, after the candidate images are displayed in steps S1 to S5 of the EXAMPLE, the user may specify target image groups on the basis of the candidate image and the bright field image and the processes of steps S107 to S111 in FIG. 10 may be performed.

Preferably, the target image groups once specified can be replaced. For example, when the user operates a prescribed operation (for example, key operation of a keyboard) after step S107 or S108, the controller 21 returns to the processing of step S105, so that the target image group is reset and specified again.

Modified Example 3

The above EXAMPLE may include the step of evaluating whether or not the candidate images prepared in step S4 composes a correct interest image. Specifically, the controller 21 evaluates whether or not the candidate image composes a correct interest image on the basis of the feature amount of the candidate images and the feature amount of the standard interest region previously stored in the storage 25.

Any known feature amount of the target image may be used, for example, perimeter length, area, moment, adaptability in elliptic approximation, length of major axis, eccentricity, ellipticity (the ratio of minor axis to major axis), shape, contrast of the bright field image at the part corresponding to each region, gradation value after gray scale conversion, average optical density, texture, and color. The evaluation value is preferably calculated by quantitating the evaluation result, so that the candidate image which is highly likely to compose the correct interest image can be easily selected on the basis of the evaluation value as described in the following.

According to the MODIFIED EXAMPLE 3, for example, the candidate image having the maximum evaluation value can be displayed in step S5 of the EXAMPLE. Furthermore, the candidate image having a smaller evaluation value than a prescribed value is preferably displayed by different color or with a message indicating the small evaluation value. It is thereby recognized that the normally-displayed candidate images have a high evaluation value and compose a correct interest image. As a result, there is an advantage that the time of the image processing can be reduced, because the user can perform processing after step S5 in the EXAMPLE selectively, only for the candidate image having low evaluation value.

In step S6 of the EXAMPLE, among the plural candidate images displayed side by side as in FIGS. 6A and 7, the candidate image having the maximum evaluation value may be displayed in the center and the candidate images having low evaluation value may be displayed at the ends. Furthermore, the evaluation value may be displayed with the candidate image in step S5 or S6 of the EXAMPLE.

As a result, the user can easily select the candidate image on the basis of the evaluation value.

The display candidate image step of selecting candidate images displayed in step S6 of the EXAMPLE may be performed on the basis of the evaluation value. For example, only the candidate images having an evaluation value larger than the prescribed value are selected and displayed in step S6.

The display candidate image step may be performed on the basis of the feature amount of the candidate images and the feature amount of the standard region of interest previously stored in the storage as follows.

Figure 11:
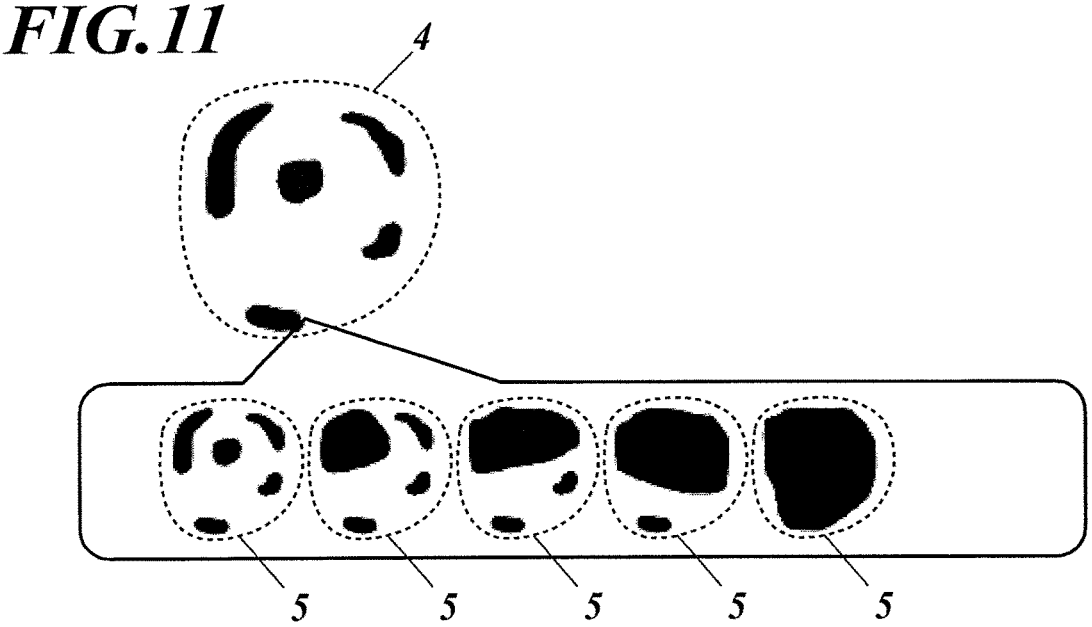
FIG. 11 is a schematic diagram illustrating an exemplary method for displaying candidate images in the MODIFIED EXAMPLE 3.

When the area of the region of interest in the candidate image displayed in step S5 is smaller than the area of the standard region of interest (in the present embodiment, region of cell), the candidate image 5 displayed in step S6 is preferably prepared by performing integration process or dilation process for the candidate image 4 displayed in step S5 (see FIG. 11). Furthermore, when the area of the region of interest in the candidate image displayed in step S5 is larger than the area of the standard region of interest, the candidate image 5 displayed in step S6 is preferably prepared by performing division process or compression process for the candidate image 4 displayed in step S5 (see FIG. 6A).

As a result of selecting the candidate images displayed in step S6 as described above, only the candidate images which are highly likely to compose the correct interest image are displayed in step S6. That is, unnecessary images are not displayed. There is an advantage that the image processing can be performed with high efficiency.

Modified Example 4

In the above EXAMPLE, for example, image processing may be performed on the basis or the fact that the expression of HER2 protein per cell can be used as an index to evaluate malignancy of cancer, specifically, on the basis of a fluorescent image representing the expression of HER2 protein extracted in step S2.

In the case of using the fluorescent bright point image in the step of setting target images in step S3 of the EXAMPLE, for example, the monochromatic image prepared in step S301 and the fluorescent bright point image are superimposed in an addition step. In steps S302 and S303, the target images are set so that all the fluorescent bright points are included in any of the target images. Such setting is preferred because it reduces the risk that a cell partly deviates from a target image.

In the case of using the fluorescent bright point image in the preparation step of candidate image in step S4 of the EXAMPLE, for example, the candidate images may be prepared so that the fluorescent bright points are distributed near the outline of the regions of interest, on the basis of the fact that the fluorescent bright points representing the expression of HER2 protein, which is a membrane protein, are often distributed near the outline of cells. Preparation of an interest image can be thereby performed with higher accuracy.

In the case of using the fluorescent bright point image in the step of displaying candidate image in step S5 of the EXAMPLE, for example, the minimum distance is calculated from each fluorescent bright point to the region of interest and summed for each of the candidate images, and the candidate image having the minimum summed value is displayed. Otherwise, for example, the density of the fluorescent bright point is calculated in the region of interest in each of the candidate images, and the candidate image having the highest density is displayed.

Figure 12A:
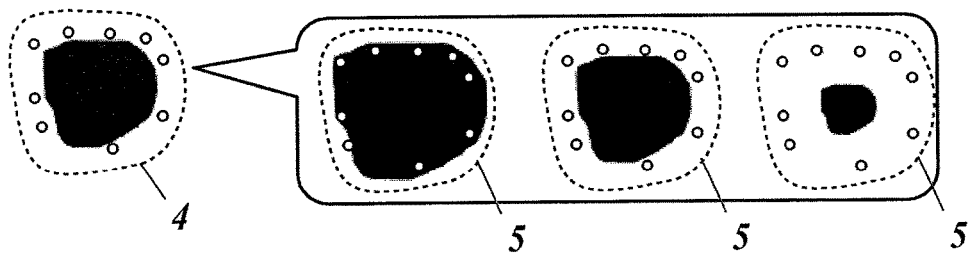
FIG. 12A is a schematic diagram illustrating an exemplary method for displaying candidate images in the MODIFIED EXAMPLE 4.
Figure 12B:
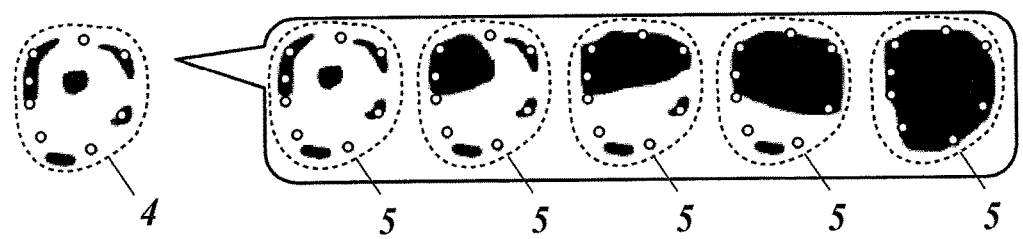
FIG. 12B is a schematic diagram illustrating an exemplary method for displaying candidate images in the MODIFIED EXAMPLE 4.

When fluorescent bright points (circle) and candidate images 4 and 5 are superimposed and displayed in step S6 of the EXAMPLE as shown in FIGS. 12A and 12B, the user can select candidate images on the basis of the distribution of the fluorescent bright point.

According to the above-described embodiments, even when automatic and highly accurate image processing is difficult (for example, in extracting cell regions from a tissue sample image), the user can select displayed candidate images for a part of the image and can easily correct only the part of the image. Highly accurate interest image can be thereby easily prepared and accurate pathological diagnosis can be carrying out.

By setting target image groups on the basis of the feature amount distribution of the target image, the controller 21 judges whether or not partial adjustment of the image is preferred. When it is judges that partial adjustment is not necessary, image processing can be performed collectively for the whole image. Even when it is determined that partial adjustment of image is necessary, specification of target image groups enables collective image processing for the target images having similar feature amount, for example. Time and cost of image processing can be thereby reduced.

Detailed modification is possible due to continuous change of the displayed candidate image via the operation of slide bar and the like.

Image processing for preparing candidate images may include changing plural parameters, i.e., at least one of luminance, chromaticity, and edge of the target image. In such cases, the candidate images may be displayed at a position corresponding to the parameter value in a multidimensional space which has different parameters on each dimensional axis. Because of the change in the display method for candidate images, the candidate image to be displayed, and the like on the basis of the evaluation result whether or not each candidate image corresponds to the correct interest image, the user can easily select candidate images which are highly likely to compose the correct interest image.

By preparing the candidate images not only using the bright field image but also using the fluorescent bright point image or by displaying the fluorescent bright points with the candidate image, the user can easily select candidate images which are highly likely to compose the correct interest image.

The description of the present embodiment is merely a suitable example of the present invention and does not limit the present invention.

For example, the EXAMPLE may be changed as follows: after setting the target images in step S3, the target images are displayed in step S5 instead of the candidate images; the user selects one of the target images; and the selected target image is subjected to the step of preparing candidate images as in step S4 of the EXAMPLE.

In the present embodiment, the exemplary final objective interest image is explained as an image in which cell region is extracted as a region of interest. Otherwise, for example, the interest image may be a fluorescent image representing the expression of a biological substance stained with a fluorescent substance. In this case, the image processing of the present invention may be performed for partial modification of the fluorescent image in order to remove noise due to contamination and the like.

The specific biological substance is HER2 protein in breast cancer in the EXAMPLE, but is not limited thereto. By changing the biological substance-recognizing site used in obtaining fluorescent images according to the pathological change (cancer) to be diagnosed, the expression of biological substance according to the type of the pathological change can be provided to medical doctors.

The target for diagnosis is a tissue slice obtained from a human body in the present embodiment, but is not limited thereto. The tissue includes a cultured tissue. Instead of the sample may be cells separated from tissue, cultured cells, cells in blood (for example, red blood cells, white blood cells, platelets, etc.), and urinary sediment.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

Other than the above, the detailed configuration and the detailed operation of each device composing the pathological diagnosis assistance system 10 can be suitably changed within the scope of the present invention.

Although embodiments of the present invention have been described and illustrated in detail, it is clearly understood that the same is by way of illustration and example only and not limitation, the scope of the present invention should be interpreted by terms of the appended claims.

INDUSTRIAL APPLICABILITY

The present invention can be preferably used in processing an image used for pathological diagnosis.

DESCRIPTION OF REFERENCE NUMERALS 1A microscopic image obtaining apparatus
2A image processing device
3A cable
10 pathological diagnosis assistance system
21 controller (a setting unit, a preparation unit, a display unit, a selection unit, a determination unit, a judging unit, an evaluation unit, a display candidate image selection unit, a specification unit, and a fluorescent bright point extraction unit)
22 operation unit
23 display
24 communication I/F (an input unit of a cell image, an input unit of a fluorescent image)
25 storage
26 bus

The invention claimed is:

1. An image processing device which prepares an interest image from an image obtained by photographing a cell in a sample, the image processing device comprising:
   a cell image inputting unit to which the image is input;
   a setting unit which sets one or more target images in the image;
   a preparation unit which prepares plural candidate images by performing image processing of each of the one or more target images using one or more prescribed parameters;
   a display which displays the plural candidate images prepared by the preparation unit; and
   a judging unit which quantitatively judges deviation of a prescribed feature amount of the image,
   wherein, when the judging unit judges that the deviation of the prescribed feature amount is larger than a prescribed reference value, the setting unit sets the plural target images based on the feature amount.

2. The image processing device according to claim 1, wherein a cell or a cell nuclei in the sample is stained.

3. The image processing device according to claim 1, wherein the preparation unit prepares the plural candidate images using the one or more parameters which continuously change according to a user operation.

4. The image processing device according to claim 1, wherein the preparation unit performs image processing using the one or more parameters including at least one of luminance, chromaticity, or edge of the target image.

5. The image processing device according to claim 1, wherein,
   the preparation unit performs image processing using plural parameters; and
   the display displays the plural candidate images arranged at a position corresponding to values of the plural parameters, wherein different parameters are set on each dimensional axis.

6. The image processing device according to claim 1, further comprising an evaluation unit which calculates an evaluation value based on at least one of area, perimeter length, circularity, and ellipticity of the plural candidate images and evaluates whether or not each of the plural candidate images composes the interest image, wherein, when the plural candidate images having different values of the parameter from each other are displayed, the display unit determines arrangement of the plural candidate images based on the evaluation value.

7. The image processing device according to claim 1, further comprising a display candidate image selection unit which selects the plural candidate images displayed on the display via a user operation, wherein the one or more parameters are within a prescribed range.

8. The image processing device according to claim 1, further comprising a specification unit to specify group of the target images, wherein the preparation unit performs image processing using the one or more parameters having same value for the target images specified as a same group.

9. The image processing device according to claim 1, wherein a specific biological substance in the sample is stained by a fluorescent particle in which a fluorescent substance is integrated, the image processing device further comprising:

a fluorescent image inputting unit to which a fluorescent image is input, which is obtained by photographing a same visual field as the image and which represents a position of the specific biological substance by a fluorescent bright point based on fluorescence of the fluorescent particle; and a fluorescent bright point extraction unit which extracts a position of the fluorescent bright point in the fluorescent image, wherein the preparation unit performs image processing using a parameter based on the plural candidate images and the position of the fluorescent bright point.

10. The image processing device according to claim 9, wherein the display superimposes and displays the plural candidate images and the fluorescent image, wherein a view field of the fluorescent image is same as a view field of the target image.

11. The image processing device according to claim 1, further comprising a selection unit which selects one of the plural candidate images according to a user operation.

12. The image processing device according to claim 11, further comprising a determination unit which determines the one of the plural candidate images selected by the selection unit to be an interest image.

13. An image processing method which prepares an interest image from an image obtained by photographing a cell in a sample, the method comprising:

inputting the image of the cell;

setting one or more target images in the image;

preparing plural candidate images by performing image processing of each of the one or more target images using one or more prescribed parameters;

displaying the plural candidate images prepared in the preparing; and quantitatively judging deviation of a prescribed feature amount of the image, wherein, when the quantitatively judged deviation of the prescribed feature amount is larger than a prescribed reference value, the setting step sets the plural target images based on the feature amount.

14. A non-transitory recording medium storing a computer readable image processing program causing a computer which prepares an interest image from an image obtained by photographing a cell in a sample, to function as:

a cell image inputting unit to which the image is input;

a setting unit which sets one or more target images in the image;

a preparation unit which prepares plural candidate images by performing image processing of each of the one or more target images using one or more prescribed parameters;

a display unit which displays the plural candidate images prepared by the preparation unit; and a judging unit which quantitatively judges deviation of a prescribed feature amount of the image, wherein, when the judging unit judges that the deviation of the prescribed feature amount is larger than a prescribed reference value, the setting unit sets the plural target images based on the feature amount.

* * * * *